(12) United States Patent
Li et al.

(10) Patent No.: US 10,772,692 B1
(45) Date of Patent: Sep. 15, 2020

(54) PROBE DEVICE, PRECISION DETECTION METHOD, PRECISION DETECTION SYSTEM, AND POSITIONING SYSTEM

(71) Applicant: Tinavi Medical Technologies Co., Ltd., Haidian District, Beijing (CN)

(72) Inventors: Yinyan Li, Beijing (CN); Bo Chen, Beijing (CN); Yubiao Wei, Beijing (CN)

(73) Assignee: TINAVI MEDICAL TECHNOLOGIES CO., LTD., Haidian District, Beijing (CN)

( * ) Notice: Subject to any disclaimer, the term of this patent is extended or adjusted under 35 U.S.C. 154(b) by 0 days.

(21) Appl. No.: 16/560,402

(22) Filed: Sep. 4, 2019

(30) Foreign Application Priority Data

Apr. 28, 2019 (CN) .......................... 2019 1 0349611

(51) Int. Cl.
*A61B 34/30* (2016.01)
*B25J 9/16* (2006.01)

(52) U.S. Cl.
CPC ............. *A61B 34/30* (2016.02); *B25J 9/1653* (2013.01); *B25J 9/1664* (2013.01); *B25J 9/1692* (2013.01)

(58) Field of Classification Search
CPC ....... A61B 34/30; B25J 9/1653; B25J 9/1664; B25J 9/1692
See application file for complete search history.

(56) References Cited

U.S. PATENT DOCUMENTS

| 5,086,401 A * | 2/1992 | Glassman | B25J 9/1679 |
| | | | 700/259 |
| 5,987,960 A * | 11/1999 | Messner | A61B 17/00 |
| | | | 73/1.79 |
| 2003/0209096 A1 * | 11/2003 | Pandey | A61B 34/20 |
| | | | 73/865.9 |
| 2004/0167654 A1 * | 8/2004 | Grimm | A61B 34/20 |
| | | | 700/114 |
| 2007/0270685 A1 * | 11/2007 | Kang | A61B 90/03 |
| | | | 600/424 |
| 2016/0256225 A1 * | 9/2016 | Crawford | A61B 90/96 |
| 2018/0014888 A1 * | 1/2018 | Bonny | A61B 34/20 |

\* cited by examiner

*Primary Examiner* — Stephen Holwerda
(74) *Attorney, Agent, or Firm* — Panitch Schwarze Belisario & Nadel LLP

(57) ABSTRACT

The invention provides a probe device, a precision detection method, a precision detection system, and a positioning system. The probe device includes a positioning part and a guide detection part, wherein the positioning part is provided with a support having three or more non-collinear positioning element installed thereon, and the guide detection part is connected with the support, has a first preset positional relation with the positioning elements, and has a cylindrical outer contour matched with a guide element of the positioning system. The precision of the guide element can be accurately detected, so that the control precision of a surgical robot is effectively improved, and the system safety is improved.

6 Claims, 6 Drawing Sheets

PROBE DEVICE, PRECISION DETECTION METHOD, PRECISION DETECTION SYSTEM, AND POSITIONING SYSTEM

CROSS-REFERENCE TO RELATED APPLICATIONS

This application claims priority under 35 U.S.C. § 119(b) to Chinese Patent Application No. 201910349611.X, filed Apr. 28, 2019, which is incorporated herein by reference in its entirety.

BACKGROUND OF THE INVENTION

1. Technical Field

The invention relates to the technical field of medical instruments, in particular to a probe device, a precision detection method, a precision detection system, and a positioning system.

2. Description of Related Art

A surgical robot is generally used for guidance during orthopedic surgery, and the precision of a guide element has a significant influence on the path planning precision. Deformation and wear of the guide element caused in the transportation, storage, sterilization or using process will affect the path planning accuracy or precision. In addition, due to the fact that the deformation and wear of the guide element are unperceivable, the guide element cannot accurately move to a preset position of a wound of patients during the surgery, which in turn affects the control precision of the whole surgical robot.

In view of this, there is a need for a novel probe device, precision detection method, precision detection system, and positioning system.

BRIEF SUMMARY OF THE INVENTION

The objective of the invention is to improve the precision of a guide element by providing a probe device, a precision detection method, a precision detection system, and a positioning system.

The invention provides a probe device used for detecting the precision of a surgical robot positioning system. The probe device includes a positioning part and a guide detection part, wherein the positioning part s provided with a support having three or more positioning elements installed thereon, and the guide detection part is connected with the support, has a first preset positional relation with the positioning elements, and has a cylindrical outer contour matched with a guide element of the positioning system.

The invention further provides a precision detection system used for detecting the precision of a surgical robot positioning system including a guide element and a calibrator. The precision detection system includes:
the probe device mentioned above;
an acquisition device used for a first set position of the guide element;
a position finder used for acquiring a position parameter of the guide detection part in the case where the guide detection part is matched with the guide element; and
a calculation device used for determining the precision of the guide element according to the first set position of the guide element and the position parameter of the guide detection part.

The invention further provides a surgical robot positioning system including a surgical robot, a host computer, a position finder, a guide element, a calibrator, and the probe device mentioned above.

The probe device of the invention includes the positioning part and the guide detection part, three or more non-collinear positioning elements are arranged on the support of the positioning part, and the guide detection part has a first preset positional relation with the positioning elements, so that the spatial position of the guide detection part can be figured out according to the positioning elements; the guide detection part is matched with the guide element through the cylindrical outer contour, so that the actual position of the guide element can be figured out according to the positional relation between the guide element and the guide detection part, and the precision of the guide element can be determined by comparison of the actual position and the first set position of the guide element. The precision of the guide element can be accurately detected, so that the control precision of the surgical robot is effectively improved.

BRIEF DESCRIPTION OF THE SEVERAL VIEWS OF THE DRAWINGS

Those skilled in the art can have a better understanding of other characteristics, objectives, and advantages of the invention by reading the following detailed description of non-restrictive embodiments with reference to the accompanying drawings, wherein identical or similar reference signs in the drawings represent identical or similar characteristics.

REFERENCE SIGNS

Figure 1:
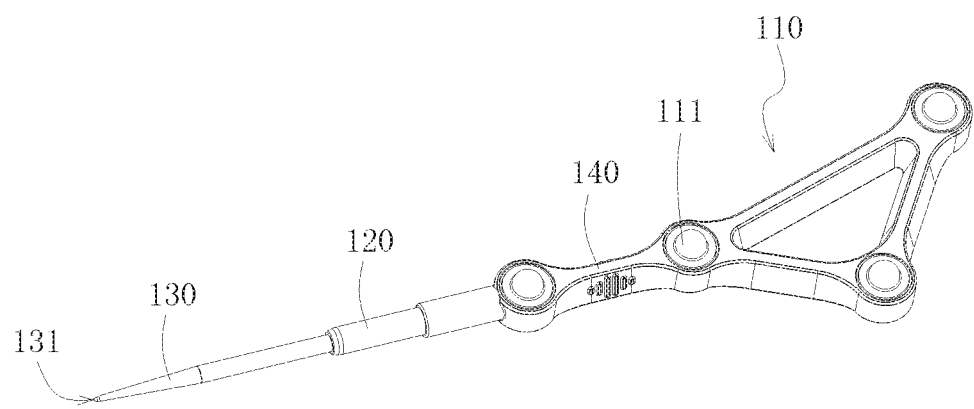
FIG. 1 is a structural diagram of a probe device in one embodiment of the invention.

100, probe device;
110, positioning part; 111, positioning element;
120, guide detection part;
130, contact tip; 131, contact ball;
140, handle;
200, guide element;
300, calibrator; 310, mark point.

DETAILED DESCRIPTION OF THE INVENTION

The characteristics and illustrative embodiments of the invention are detailed below. For a comprehensive understanding of the invention, many details are given in the following description. However, it is obvious for those skilled in the art to implement the invention without certain ones of these specific details. These illustrative embodiments in the following description are used for a better understanding of the invention. At least part of well-known structures and techniques are not shown in the accompanying drawings and the following description to avoid a fuzzy comprehension of the invention. In addition, for the sake of a clear illustration, the sizes of part of the structures are amplified. Moreover, the characteristics, structures, and properties in the following description can be appropriately integrated in one or more embodiments.

In the description of the invention, unless otherwise noted, "multiple" refers to two or more; and the directional or positional relations indicated by the terms "upper", "lower", "left", "right", "inner", and "outer" are used for facilitating and simplifying the description of the invention, and do not indicate or hint that devices or elements referred to must have specific directions or must be configured or operated in specific directions, and thus, these terms should not be interpreted as limitations on the invention. Moreover, the terms such as "first" and "second" are only for the purpose of description, and do not indicate or hint the relative importance of devices or elements referred to.

All directional terms involved in the following description refer to directions shown in the drawings and are not intended to limit the specific structures of the embodiments of the invention. What should to be pointed out is that unless otherwise explicitly specified or limited, the terms "install" and "connect" should be broadly appreciated. For instance, the term "connect" may refer to "fixed connection", "detachable connection", "integral connection", "direct connection", or "indirect connection". Those ordinarily skilled in the art can appreciate the specific meanings of these terms in the invention as the case may be.

For a better understanding of the invention, a detailed description of the probe device, the precision detection method, the precision detection system, and the positioning system of the embodiments of the invention is given below with reference to FIGS. 1-8.

Figure 2:
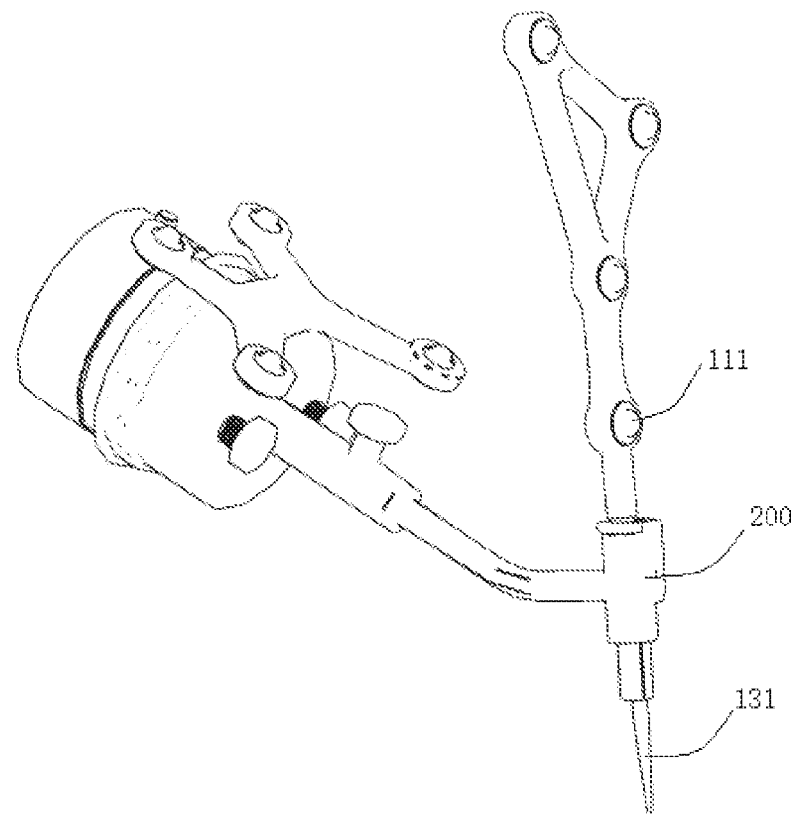
FIG. 2 is a cooperation structural diagram of the probe device and a guide element in one embodiment of the invention.

Please refer to FIG. 1 and FIG. 2, wherein FIG. 1 is a structural diagram of the probe device 100 in the first embodiment of the invention, and FIG. 2 is a cooperative structural diagram of the probe device 100 and a guide element 200. The probe device 100 is used for a surgical robot positioning system which generally includes a guide element 200, a position finder, a calibrator 300, and the like. The probe device 100 includes a positioning part 110 and a guide detection part 120, wherein the positioning part 110 is provided with a support having three or more non-collinear positioning elements 111 installed thereon, and the guide detection part 120 is connected with the support, has a first preset positional relation with the positioning elements 111, and has a cylindrical outer contour matched with the guide element 200 of the positioning system.

Wherein, the number of the positioning elements 111 on the support is not limited and can be three, four, or more. For instance, as shown in FIG. 1, four positioning elements 111 are configured, and at least three of the four positioning elements 111 are not collinear, so that the position finder can accurately figure out the spatial position of the guide detection part 120 according to the three or more positioning elements 111.

The specific configuration of the positioning elements 111 is not limited. For instance, the positioning elements 111 are infrared reflection balls capable of reflecting infrared rays to be recognized by the position finder; or, the positioning elements 111 are infrared emitters capable of emitting infrared rays, and the position finder can recognize the infrared rays so as to recognize the positioning elements 111. Other configurations are also feasible as long as the positioning elements 111 can be recognized by the position finder.

The probe device 100 of the invention includes the positioning part 110 and the guide detection part 120, wherein three or more non-collinear positioning elements 111 are installed on the support of the positioning part 110, and the guide detection part 120 has a first preset positional relation with the positioning elements 111, so that the spatial position of the guide detection part 120 can be figured out according to the positioning elements 111; the guide detection part 120 is matched with the guide element 200 through the cylindrical outer contour, so that the actual position of the guide element 200 can be figured out based on the positional relation between the guide element 200 and the guide detection part 120; and the precision of the guide element 200 can be determined by comparison of the actual position and the set position of the guide element 200. In this way, the probe device in this embodiment can accurately detect the precision of the guide element 200, and thus, the control precision of the surgical robot is effectively improved.

In the using process of the probe device 100 and the surgical robot positioning system, the positioning system can control the guide element 200 to move to a preset position; when the guide detection part 120 is matched with the guide element 200, the actual position of the guide element 200 can be figured out according to the spatial position of the guide detection part 120; and the precision of the guide element 200 can be determined by comparison of the actual position and the set position of the guide element 200. The probe device 100 of the invention can detect the precision of the guide element 200, so that the situation that the control precision of the surgical robot is affected due to poor precision of the guide element 200 is prevented.

The guide detection part 120 can be matched with the guide element 200 in various ways. For instance, the guide detection part 120 is attached to the guide element 200, and in this case, in order to make sure that the guide detection part 120 can be matched with the guide element 200 more tightly, the guide detection part 120 and the guide element 200 are matched in a sleeved manner. Particularly, one of the guide detection part 120 and the guide element 200 is a cylindrical body, and the other one is a sleeve matched with the cylindrical body.

The guide element 200 is usually a guide cylinder, and in this case, the guide detection part 120 is cylindrical and has an outer circumferential surface matched with the guide cylinder, so that the guide detection part 120 can be matched with the guide element 200 through the outer circumferential surface.

The surgical robot positioning system usually further includes a calibrator 300 used for auxiliary positioning of the surgical robot. The precision of the calibrator 300 is an important factor of the planning precision of a surgical path, and the deformation and wear of the calibrator 300 caused in the transportation, storage, sterilization, and using process will affect the path planning accuracy or precision, in view of this, a mark point 310 is set on the calibrator 300, wherein the position of the mark point 310 is known or is measured, for instance, through a tracer in a positional relation with the mark point 310 particularly in such a manner: the positioning system can acquire the position of the tracer through the position finder so as to acquire the spatial position of the mark point 310, and then the set position of the mark point 310 is obtained.

Figure 3:
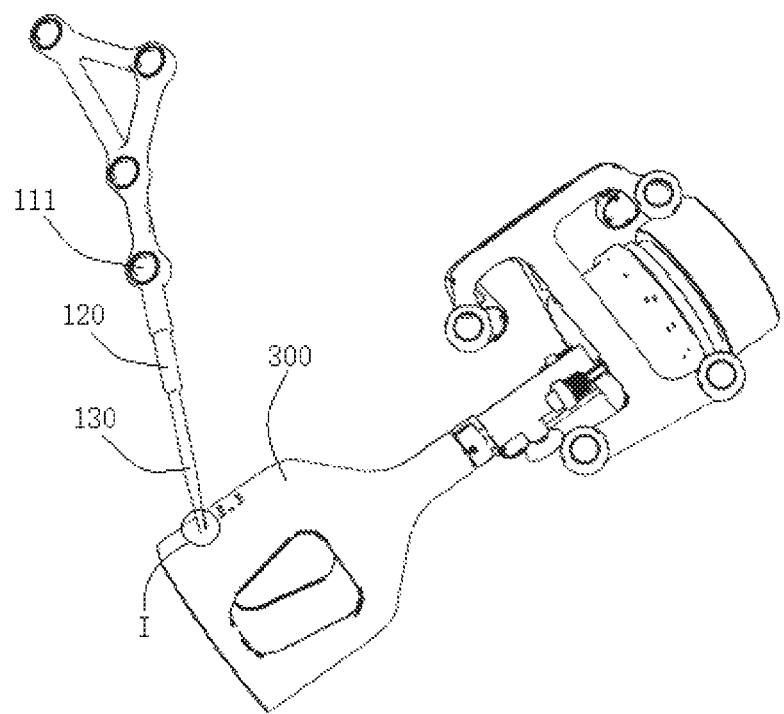
FIG. 3 is a cooperation structural diagram of the probe device and a calibrator in one embodiment of the invention.

Also referring to FIG. 3, in certain optional embodiments, the probe device 100 further includes a contact tip 130, wherein the contact tip 130 is connected with the positioning part 110, has a second preset positional relation with the positioning elements 111, and is able to make contact with the mark point 310 on the calibrator 300 of the positioning system to acquire position information of the mark point 310.

In these optional embodiments, the contact tip 130 has a second preset positional relation with the positioning elements 111, so that the spatial position of the contact tip 130 can be figured out according to the spatial positions of the positioning elements 111; and the contact tip 130 is able to make contact with the mark point 310, so that the actual position of the mark point 310 can be figured out according to the spatial position of the contact tip 130. The precision of the mark point 310, namely the precision of the calibrator 300, can be determined by comparison of the actual position and the set position of the mark point 310. In these optional embodiments, the precision of the calibrator 300 can be detected through the contact tip 130.

Figure 4:
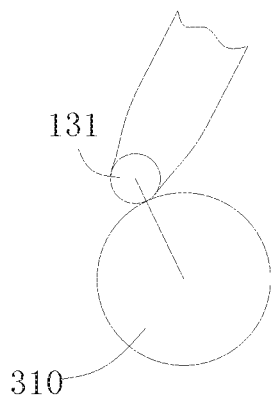
FIG. 4 is an enlarged view of part I in FIG. 3.

Also referring to FIG. 4, the contact tip 130 can make contact with the mark point 310 in various ways. In certain optional embodiments, a contact ball 131 is arranged at the top of the contact tip 130, and the contact tip 130 makes contact with the mark point 310 through the contact ball 131. In order to reduce the detection error, the radius of the contact ball 131 is greater than or equal to 0.2 mm and is smaller than or equal to 0.5 mm.

In any one of the above embodiments, the relative positions of the contact tip 130 and the guide detection part 120 are not limited. For instance, the contact tip 130 and the guide detection part 120 are respectively arranged on two sides of the positioning part 110 or, as shown in FIG. 1, the contact tip 130 and the guide detection part 120 are located on one side of the positioning part 110, and the contact tip 130 is connected with the positioning part 110 through the guide detection part 120.

In certain optional embodiments, the probe device 100 further includes a handle 140, and the probe device 100 can be operated and held through the handle 140. The configuration position of the handle 140 is not limited. In certain optional embodiments, the handle 140 is connected between two adjacent positioning elements 111, so that the size of the probe device 100 can be effectively reduced, and the structure of probe device 100 can be simplified.

Figure 5:
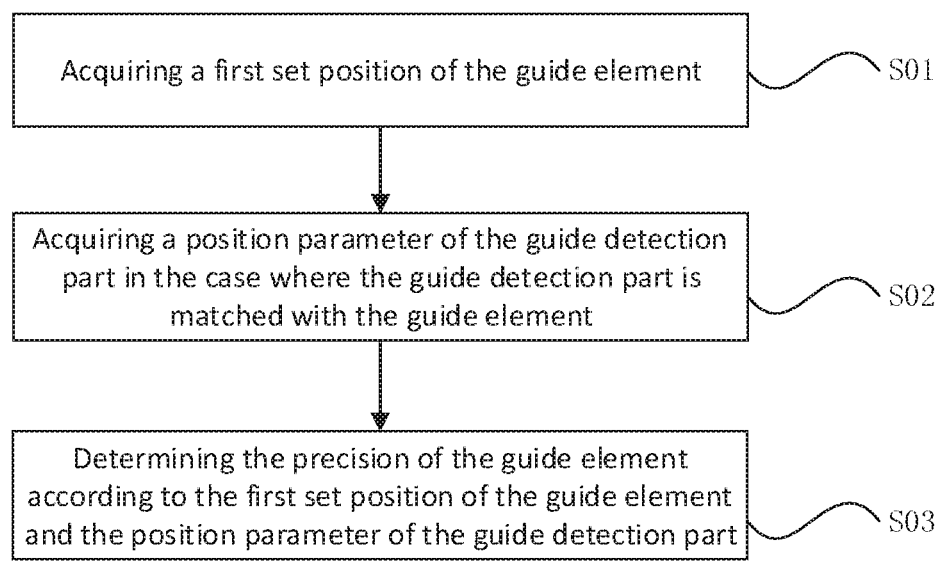
FIG. 5 is a flow diagram of a precision detection method in one embodiment of the invention.

Also referring to FIG. 5, the second embodiment of the invention provides a precision detection method for a surgical robot positioning system. The positioning system includes a guide element 200 used for guiding the surgical needle, and a calibrator 300. The precision detection method is based on the probe device 100 in the first embodiment and includes the following steps:

S01: a first set position of the guide element 200 is acquired.

The positioning system usually includes a host computer used for controlling a mechanical arm to move along a planned path so as to drive the guide element 200 to move. The position of the guide element 200 is prestored in the host computer, or is measured, for instance, through a tracer in a preset positional relation with the guide element 200 particularly in such a manner: the position of the tracer is acquired by the position finder, and then the position of the guide element 200 is acquired.

S02, a position parameter of the guide detection part 120 in the case where the guide detection part 120 is matched with the guide element 200 is acquired.

The guide detection part 120 is made to be matched with the guide element 200, and then the position parameter of the guide detection part 120 can be figured out according to the positioning elements 111 and the first preset positional relation.

S03, the precision of the guide element 200 is determined according to the first set position of the guide element 200 and the position parameter of the guide detection part 120.

Wherein, the guide element 200 is matched with the guide detection part 120, so that the actual position of the guide element 200 can be figured oust according to the position parameter of the guide detection part 120, and then the precision of the guide element 200 can be determined by comparison of the actual position and the first set position (theoretical position) of the guide element 200. In this way, the precision of the guide element 200 is determined according to the position parameter of the guide detection part 120 and the first set position.

According to this embodiment, in S01; the first set position of the guide element 200 is acquired; in S02, the position parameter of the guide detection part 120 is figured out according to three or more positioning elements 111 and the first preset positional relation in the case where the guide detection part 120 is matched with the guide element 200; and in S03, the precision of the guide element 200 is determined by comparison of the first set position of the guide element 200 and the position parameter of the guide detection part 120. In this way, the precision of the positioning system is determined.

The first set position of the guide element 200 can be any position of the guide element 200 meeting the requirement for figuring out the spatial position of the guide element 200. The guide element 200 is generally cylindrical. In certain optional embodiments, the first set position includes center positions of two Opposite axial end faces of the guide element 200, so that the first set position can be accurately searched out and located, Wherein, a connection line between the centers of the two end faces is defined as a mark axis.

The position parameter of the guide detection part 120 can be the spatial position of a specified axis of the guide detection part 120. Due to the fact that the guide element 200 is in a cooperative positional relation with the guide detection part 120 when matched with the guide detection part 120, the position of mark axis has a cooperative positional relation with that of the specified axis.

Generally, the guide detection part 120 and the guide element 200 are matched in a sleeved manner, in this case, the central axis of the guide detection part 120 theoretically coincides with the central axis of the guide element 200, so, if the specified axis of the guide detection part 120 is set as the central axis of the guide detection part 120, the position of the central axis is the actual position of the mark axis. In this way, the comparison process can be simplified, and the precision of the guide element 200 can be determined more easily according to the positional relation of the two axes.

The support and the guide detection part 120 can be in any positional relations as long as the first preset positional relation is presented between the positioning elements 111 and the guide detection part 120, and the invention has not limitation in this aspect. Preferably, the specified axis of the guide detection part 120 (such as the central axis of the guide detection part 120) and the support are coplanar, so that the relative positional relation between the support and the specified axis of the guide detection part 120 can be determined easily.

In the case where the guide detection part 120 is matched with the guide element 200, the position parameter of the guide detection part 120 can be determined in various ways. In certain optional embodiments, S02 includes the following steps:

step (a): in the case where the guide detection part 120 and the guide element 200 are sleeved and attached together, n axis data corresponding to the specified axis of the guide detection part 120 at multiple rotation positions, which are formed when the guide detection part 120 rotates on the guide element 200, are acquired, wherein n is greater than or equal to four;

step (b): four or more axis data are selected from the n axis data to be used as fitting data; and step (c): the four or more fitting data are fitted to obtain a fitted axis data to be used as the position parameter of the guide detection part 120.

Wherein, the four or more fitting data can be fitted in various ways to form the fitted axis data. For instance, the four or more fitting data are fitted through a least square method to form the fitted axis data.

In these optional embodiments, if the guide detection part 120 and the guide element 200 cannot be entirely attached due to wear or deformation of the guide element 200, the guide detection part 120 will rotate within the guide element 200, multiple different position parameters of the guide detection part 120 may be acquired, and in view of this, n axis data are acquired. With reference to the fined axis data formed by fitting four or more of the n axis data, the detection error can be reduced, and the detection result can be more accurate.

The distance from the specified axis of the guide detection part 120 to the two ends of the guide element 200 should meet a detection deviation value. Thus, in order to further improve the precision of the detection result, step (a) includes the following step:

In the case where the guide detection part 120 and the guide element 200 are sleeved and attached together, n axis data, meeting a first detection deviation value, corresponding to the specified axis of the guide detection part 120 at the multiple rotation positions, which are formed when the guide detection part 120 rotates on the guide element 200, are acquired.

Wherein, meeting the detection deviation means the distances from the actual positions of the specified axis of the guide detection part 120 at the multiple rotation positions determined according to the positioning elements 110 to two endpoints of the first set position of the guide element are smaller than or equal to the first detection deviation value. The first detection deviation value is not limited and can be, for instance, 3 mm, 2 mm, and 1 mm.

The guide element 200 is generally cylindrical, has a preset length in the axial direction, and is used for providing a spatial path for a guide pin, and thus, the position of the axis of the guide element 200 directly reflects the precision of the guide element 200. Due to the fact that the first set position is a theoretical measurement position of the guide element 200, the first set position is usually set as the axis of the guide element 200; and if the first set position includes the center positions of the two opposite end faces of the guide element 200, the two endpoints of the first set position are the centers of the two opposite end faces of the guide element 200.

Invalid data, having the distances to the centers of the two opposite end faces of the guide element 200 being too large, may exist in all the axis data corresponding to the specified axis at the multiple rotation positions due to detection errors. In this embodiment, the n axis data, having the distances to the two endpoints of the first set position being smaller than the first detection deviation value, are selected from all the axes, and invalid axes are removed, so that the detection precision of the guide element 200 is further improved.

In other optional embodiments, in order to further improve the accuracy of the detection result, S02 includes the following steps:

step (d): data, other than the fitting data, in the n axis data are determined as detection data;

step (e): the number m of axis data, having distances to the fitted axis data meeting a first preset distance threshold and having angles with the fitted axis data meeting a preset angle threshold value in the detection data is determined;

step (f): different fitting data are selected from the n axis data in a first preset time period and are fitted to form multiple fitted axis data, and multiple values of m are determined according to the multiple fitted axis data and the corresponding detection data; and step (g): the maximum value $m_{max}$ of m is selected from the multiple values, and the fitted axis data corresponding to the maximum value $m_{max}$ is determined as a standard axis data which is used as the position parameter of the guide detection part 120.

The standard axis data corresponds to the maximum value of m, this means that there are the largest number of detection data having the distances to the standard axis data meeting the first preset distance threshold and having the angles with the standard axis data meeting the preset angle threshold value, and in this case, the standard axis data is closest to the actual position of the guide element 200. With reference to the standard axis data, few errors will be caused, and the accuracy of the detection result is further improved.

Figure 6:
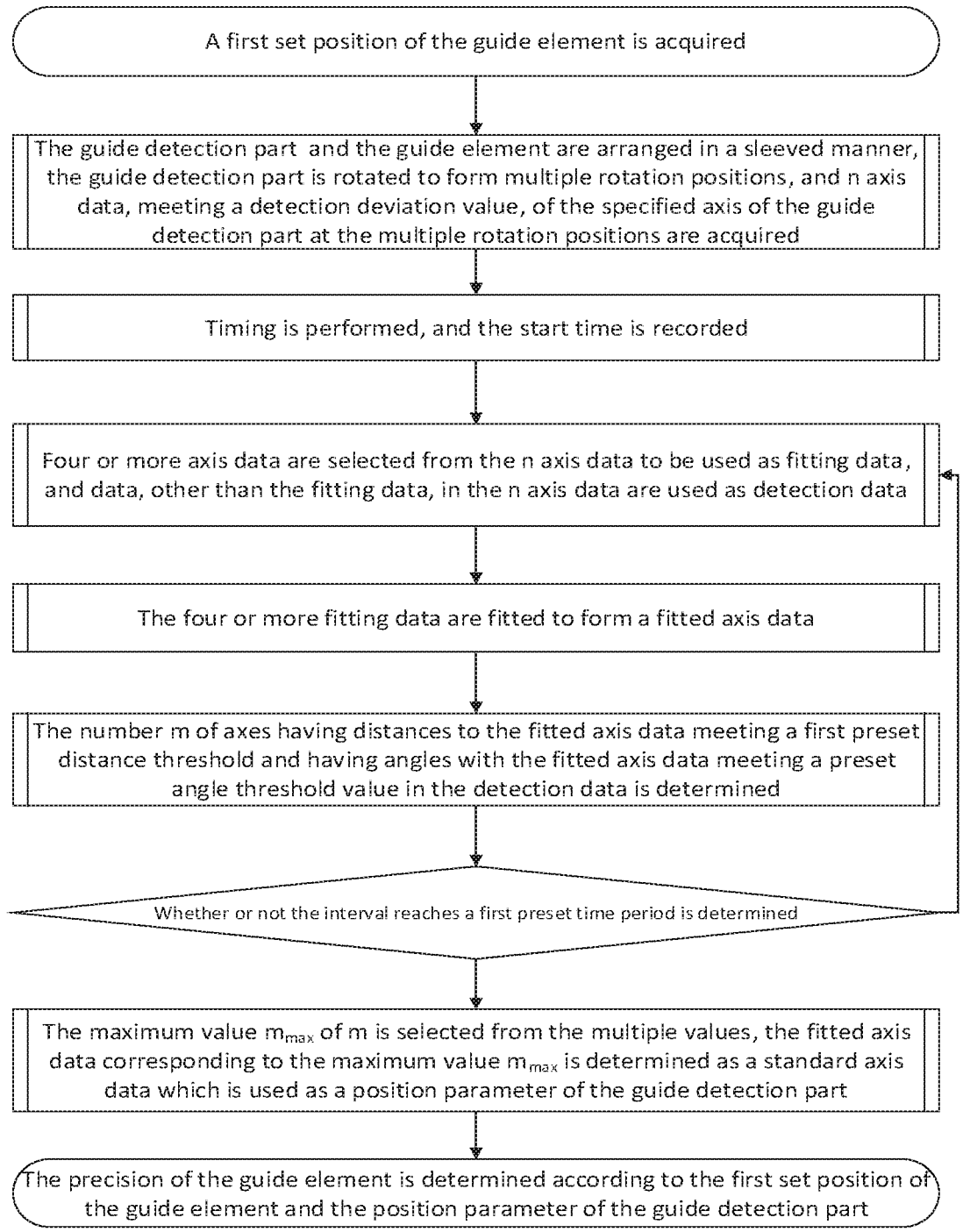
FIG. 6 is a flow diagram of the precision detection method in another embodiment of the invention.

For instance, as shown in FIG. 6, when used for detecting the guide element 200, the method specifically includes the following steps:

Step 1: a first set position of the guide element 200 is acquired.

Step 2: the guide detection part 120 and the guide element 200 are arranged in a sleeved manner, the guide detection pail 120 is rotated to form multiple rotation positions, and n axis data, meeting a detection deviation value, of the specified axis of the guide detection part at the multiple rotation positions are acquired, wherein n is greater than or equal to four.

Wherein, the specified axis is the central axis of the guide detection part 120, the first set position includes the center positions of two opposite end faces of the guide element 200, and the specified axis theoretically coincides with a connection line between the centers of the two end faces of the guide element 200, namely the axis of the guide element 200. In this case, the n axis data of the specified axis correspond to n actual axis data of the guide element 200.

Step 3: tuning is performed, and the start time is recorded. The calculation is controlled to be finite by timing, so that the precision detection cycle is reasonably controlled.

Step 4: four or more axis data are selected from the n axis data to be used as fitting data, and data, other than the fitting data, in the n axis data are used as detection data.

Step 5: the four or more fitting data are fitted to form a fitted axis data.

Step 6: the number m of axis data having distances and angles to the fitted axis data meeting first preset distance threshold value and preset angle threshold value in the detection data is determined.

Step 7: the current time is determined, and whether or not an interval from the start time to the current time meets a first preset time period is determined;

If the interval is smaller than the first preset time period, Step 4, Step 5, and Step 6 are performed again; or, if the interval is greater than or equal to the first preset time period, multiple values of m are acquired, and Step 8 is performed.

Step 8: the maximum value $m_{max}$ of m is selected from the multiple values, the fitted axis data corresponding to the maximum value $m_{max}$ is determined as a standard axis data which is used as a position parameter of the guide detection part 120.

Step 9: the precision of the guide element 200 is determined according to the first set position of the guide element 200 and the position parameter of the guide detection part 120. For instance, the distance from the midline point of the guide element 200 to the standard axis is calculated to evaluate the precision of the positioning system.

Figure 7:
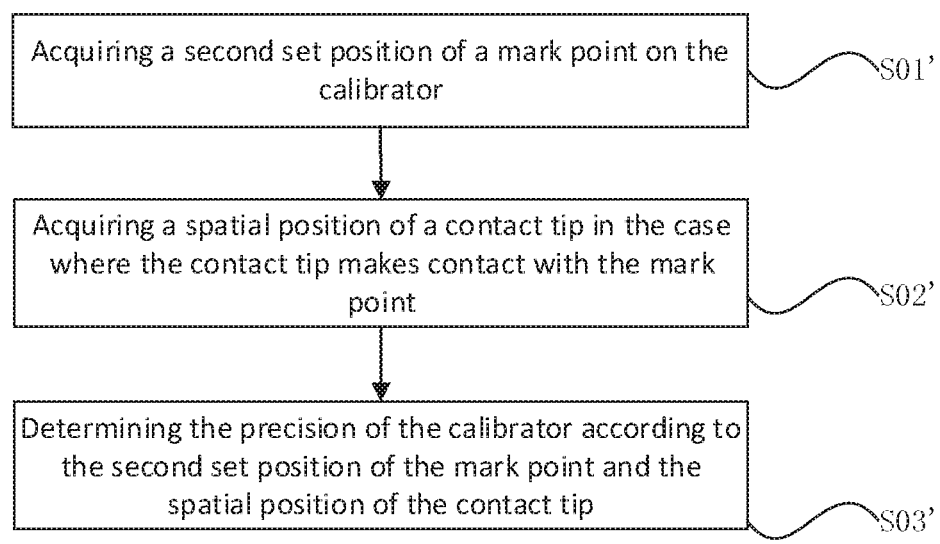
FIG. 7 is a flow diagram of the precision detection method in another embodiment of the invention.

Also referring to FIG. 7, in certain optional embodiments, the probe device 100 further includes a contact tip 130 connected with the calibrator 300 and having a second preset positional relation with the positioning elements 111, and in this case, the method further includes following steps:

S01': a second set position of the mark point 310 on the calibrator 300 is acquired.

Wherein, the second set position is the theoretical measurement position of the mark point 310 and is prestored in the host computer, or is acquired through a tracer in a preset positional relation with the calibrator 300 particularly in such as manner: the position finder acquires the spatial position of the tracer, and then the spatial position of the calibrator 300 is acquired.

S02': the spatial position of the contact tip 130 in the case where the contact tip 130 makes contact with the mark point 310 is acquired.

The spatial position of the contact tip 130 can be figured out according to the positioning elements 111 and the second preset positional relation.

S03': the precision of the calibrator 300 is determined according to the second set position of the mark point 310 and the spatial position of the contact tip 130.

Due to the fact that the contact tip 130 directly makes contact with the mark point 310, the spatial position of the contact tip 130 can be considered as the actual position of the mark point 310. Thus, the precision of the calibrator 300 can be accurately determined by comparison of the second set position and actual position of the mark point in S03'.

In certain optional embodiments, in order to improve the accuracy of the detection result, S02' includes the following steps:

step (a'): p spatial position data of the contact tip 130 and the mark point 310 at multiple contact positions are acquired, wherein p is greater than or equal to four.

step (b'): four or more spatial position data are selected from the p spatial position data to be used as fitting point data.

step (c'): the four or more fitting point data are fitted to form a virtual ball which is used as the spatial position of the contact tip 130.

Wherein, the distances from some of the multiple spatial positions acquired at the multiple contact positions to the center, namely the second set position, of the mark point 310 are greater than or equal to a second detection deviation value, and in order to further improve the accuracy of the detection result, the spatial positions not meeting the second detection deviation value should be removed after the spatial positions of the contact tip 130 at multiple contact positions are determined, and only p spatial position data meeting the second detection deviation value are reserved. Thus, in certain optional embodiments, step (a') includes the following step:

p spatial position data having distances to the second set position being smaller than the second detection deviation value are acquired from all the spatial position data of the contact tip 130 and the mark point 310 at the multiple positions.

The second detection deviation value can be set in various ways. For instance, the second preset distance value is 1 mm, 2 mm, 4 mm, 5 mm, 6 mm, or the like.

In order to further improve the accuracy of the detection result, S02' includes:

step (d'): spatial position data, other than the fitting point data, in the p spatial position data are determined as detection point data.

step (e'): the number q of detection point data having distances to the virtual ball meeting the second preset distance threshold in the multiple detection point data is determined.

step (f'): different fitting point data are selected from the p spatial position data in a second preset time period and are fitted to form multiple virtual balls, and multiple values of q are determined according to the multiple virtual balls and the corresponding detection point data.

step (g'): the maximum value $q_{max}$ of q is selected from the multiple values, and the virtual ball corresponding to the maximum value $q_{max}$ is determined as a standard ball which is used as the spatial position of the contact tip 130.

When the number of detection points corresponding to the virtual ball is large, it indicates that the virtual ball is close to the actual position of the mark point 310. The virtual ball corresponding to the maximum value $q_{max}$ is used as the standard ball, and the spatial position of the contact tip 130 is set as the spatial position of the standard ball, so that the accuracy of the detection result is further improved.

Wherein, the virtual ball can be formed in various ways. For instance, the four or more fitting point data are fitted through a least square method to form the virtual ball.

Figure 8:
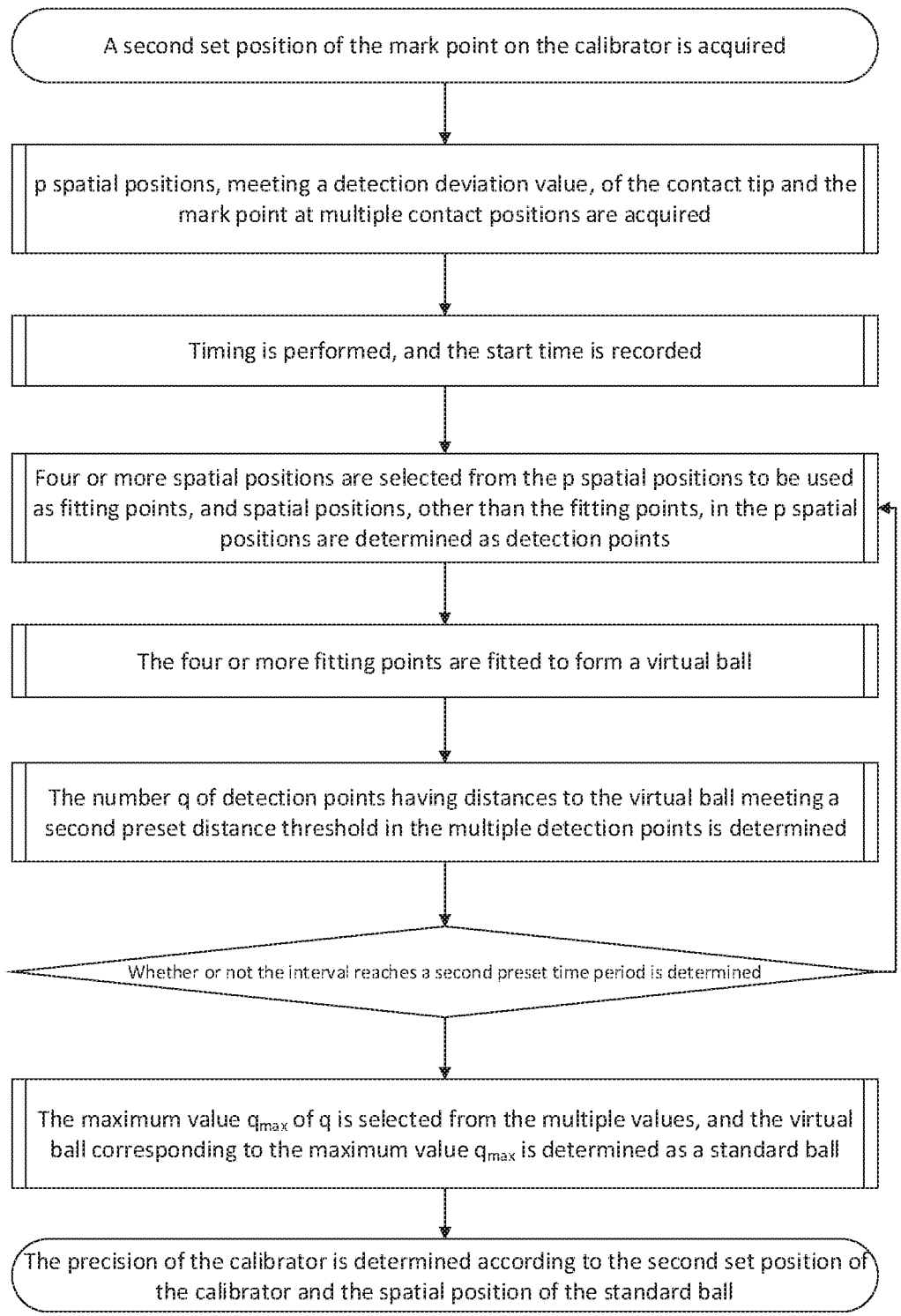
FIG. 8 is a flow diagram of the precision detection method in another embodiment of the invention.

For instance, as shown in FIG. 8, when used for detecting the calibrator 300, the method includes the following detection steps:

Step 1: a second set position of the mark point 310 on the calibrator 300 is acquired.

Step 2: p spatial position data, meeting a detection deviation value, of the contact tip 130 and the mark point 310 at multiple contact positions are acquired, wherein p is greater than or equal to four;

Step 3: timing is performed, and the start time is recorded. The calculation is controlled to be finite by timing, so that the precision detection cycle is reasonably controlled.

Step 4: four or more spatial position data are selected from the p spatial position data to be used as fitting point data, and spatial position data, other than the fitting point data, in the p spatial position data are determined as detection point data.

Step 5: the four or more fitting point data are fitted to form a virtual ball.

Step 6: the number q of detection point data having distances to the virtual ball meeting a second preset distance threshold in the multiple detection point data is determined.

Step 7: the current time is determined, and whether or not an interval from the start time to the current time meets a second preset time period is determined;

If the interval is smaller than the second preset time period, Step 4, Step 5 and Step 6 are performed again; or, if the interval is greater than or equal to the second preset time period, multiple values of q are acquired, and Step 8 is performed.

Step 8: the maximum value $q_{max}$ of q is selected from the multiple values, and the virtual ball corresponding to the maximum value $q_{max}$ is determined as a standard ball.

Step 9: the precision of the calibrator 300 is determined according to the second set position of the calibrator 310 and the spatial position of the standard ball.

The third embodiment of the invention provides a precision detection system for a surgical robot positioning system including a guide element 200 and the calibrator 300. The precision detection system includes: any of the probe device 100 in the first embodiment;

an acquisition device used for acquiring a first set position of the guide element 200;

a position finder used for acquiring a position parameter of a guide detection part 120 in the case where the guide detection part 120 is matched with the guide element 200; and a calculation device used for determining the precision of the guide element 200 according to the first set position of the guide element 200 and the position parameter of the guide detection part 120.

The precision detection system in this embodiment adopts any of the probe devices 100 in the first embodiment. The probe device 100 includes a positioning part 110 and a guide detection part 120, wherein three or more non-collinear positioning elements 111 are installed on a support of the positioning part 110, and the spatial position of the support can be figured out according to the three or more positioning elements 111. The acquisition device can acquire the first preset position of the guide element 200, namely the preset position of the guide element 200; the position finder can acquire the position parameter of the guide detection part 120; the guide detection part 120 can be matched with the guide element 200 through a cylindrical outer contour of the guide detection part 120, so that the actual position of the guide element 200 can be figured out according to the positional relation of the guide detection part 120; and the calculation device can determine the precision of the guide element 200 by comparison of the first set position of the guide element 200 and the position parameter of the guide detection part 120, namely the preset position and the actual position of the guide element 200. Thus, the precision of the guide element 200 can be accurately detected automatically, and the control precision of the surgical robot is effectively improved.

In certain optional embodiments, the probe device 100 further includes a contact tip 130, and the contact tip 130 is connected with the positioning part 110 and has a second preset positional relation with the positioning elements 111. The acquisition device is also used for acquiring a second set position of a mark point 310 on the calibrator 300, the position finder is also used for acquiring the spatial position of the contact tip 130 in the case where the contact tip 130 makes contact with the mark point 310, and the calculation device is also used for determining the precision of the calibrator 300 according to the second set position and the spatial position of the contact tip 130. Thus, in these optional embodiments, the probe device 100 can also detect the precision of the calibrator 300.

In certain optional embodiments, in order to fulfill full-automatic precision detection, the acquisition device includes a tracer, and the tracer is used for acquiring the set positions of the guide element 200 and the calibrator 300 in cooperation with the position finder.

In these optional embodiments, the tracer in a preset positional relation with the guide element 200 or the calibrator 300 is configured, and the position finder acquires the set positions of the guide element 200 and the calibrator 300 by acquiring the position of the tracer.

In the using process of the precision detection system, the tracer is in a preset positional relation with the guide element 200 and/or the calibrator 300; when the guide element 200 and/or the calibrator 300 are/is worn or deformed, the preset positional relation between the tracer and the guide element 200 and/or the calibrator 300 will change, the position finder can acquire the set position of the guide element 200 and/or the calibrator 300 through the tracer and can also acquire the spatial position of the guide detection part 120 and/or the contact tip 130, and the spatial position of the guide detection part 120 acrd/or the contact tip 130 are/is the actual position of the guide element 200 and/or the calibrator 300; and the calculation device can accurately measure the precision of the guide element 200 and/or the calibrator 300 by comparing the set position and the actual position of the guide element 200 and/or the calibrator 300.

The fourth embodiment of the invention provides a positioning system. The positioning system includes a surgical robot, a host computer, a position finder, a guide element 200, a calibrator 300, and a probe device 100 in any of the embodiments mentioned above.

During orthopedic surgery, the guide element 200 and the calibrator 300 are used for auxiliary guidance and positioning of the surgical robot, the host computer is used for controlling the surgical robot to drive the guide element 200 and the calibrator 300 to move, the position finder is used for acquiring the set positions of the guide element 200 and the calibrator 300 and is also used for recognizing three or more positioning elements 111 and determining the spatial position of a support according to the three or more positioning elements 111, and then the spatial position of the guide detection part 120 is figured out.

The position finder can be configured in various ways. For instance, the position finder is an infrared receiver used for receiving an infrared signal emitted by the tracer in a preset positional relation with the positioning elements 111; or, the position finder includes an infrared receiver and an infrared emitter, the tracer is an infrared reflector, the infrared emitter emits an infrared signal, the tracer reflects the infrared signal, and the infrared receiver receives the infrared signal reflected by the positioning elements 111.

The calibrator 300 can be configured in various ways. In certain optional embodiments, a mark point 310 is set on the calibrator 300, a body of the calibrator 300 is made from materials pervious to X-rays, and the mark point 310 is made from materials not pervious X-rays, so that the position of the mark point 310 on an image can be figured out during image registration.

In addition, a position calibrator (such as a tracer) is further arranged on the calibrator 300 and has a preset positional relation with the mark point 310, so that the position finder can determine the target position of the mark point 310, namely the spatial coordinates of the mark pint 310, by acquiring the spatial position coordinates of the position calibrator.

The invention can also be implemented in other forms without deviating from its spirit and substantive characteristics. For instance, the methods involved in specific embodiments can be modified on the basis that the system structure does not deviate from the basic spirit of the invention. Thus, all these embodiments mentioned above should be regarded as illustrative ones instead of restrictive ones. The scope of the invention is defined by the claims instead of the above description. In addition, all variations achieved based on the claims and their equivalents should also fall within the scope of the invention.

What is claimed is:

1. A precision detection method for a surgical robot positioning system including a guide element and a calibrator, the method adopting a probe device being used for detecting precision of a surgical robot positioning system, the device comprising:
   a positioning part, provided with a support supporting three or more non-collinear positioning elements; and
   a guide detection part, connected with the support, having a first preset positional relation with the positioning elements, and having a cylindrical outer contour matched with a guide element of the positioning system,
   the method comprising:
   acquiring a first set position of the guide element;
   acquiring a position parameter of the guide detection part in a case where the guide detection part is matched with the guide element; and
   determining precision of the guide element according to the first set position of the guide element and the position parameter of the guide detection part,
   wherein the acquiring a position parameter of the guide detection part in a case where the guide detection part is matched with the guide element comprises:
   acquiring n axis data corresponding to a specified axis of the guide detection part at multiple rotation positions formed when the guide detection part rotates on the guide element in a case where the guide detection part and the guide element are sleeved and attached together, wherein n is greater than or equal to four;
   using four or more axis data selected from the n axis data as fitting data; and
   fitting the four or more fitting data to form a fitted axis data used as the position parameter of the guide detection part;
   determining data, other than the fitting data, in the n axis data as detection data;
   determining a number m of axis data having distances to the fitted axis data meeting a first preset distance threshold and having angles with the fitted axis data meeting a preset angle threshold, in the detection data;
   fitting different fitting data selected from the n axis data within a first preset time period to form multiple fitted axis data, and determining multiple values of m according to the fitted axis data and the corresponding detection data; and
   selecting a maximum value $m_{max}$ of m from the multiple values, and determining the fitted axis data corresponding to the maximum value $m_{max}$ as a standard axis data used as the position parameter of the guide detection part.

2. The method according to claim 1, wherein the first set position of the guide element includes center positions of two opposite axial end faces of the guide element.

3. The method according to claim 1, wherein the acquiring n axis data corresponding to a specified axis of the guide detection part at multiple rotation positions formed when the guide detection part rotates on the guide element in a case where the guide detection part and the guide element are sleeved and attached together comprises:
   acquiring n axis data, meeting a first detection deviation value, of the specified axis of the guide detection part at the multiple rotation position formed when the guide detection part rotates on the guide element in the case where the guide detection part and the guide element are sleeved and attached together.

4. A precision detection method for a surgical robot positioning system including a guide element and a calibrator, the method adopting a probe device being used for detecting precision of a surgical robot positioning system, the device comprising:
   a positioning part, provided with a support supporting three or more non-collinear positioning elements; and
   a guide detection part, connected with the support, having a first preset positional relation with the positioning elements, and having a cylindrical outer contour matched with a guide element of the positioning system,
   the method comprising:
   acquiring a first set position of the guide element;
   acquiring a position parameter of the guide detection part in a case where the guide detection part is matched with the guide element; and
   determining precision of the guide element according to the first set position of the guide element and the position parameter of the guide detection part;
   acquiring a second set position of a mark point on the calibrator;
   acquiring a spatial position of the contact tip in a case where the contact tip makes contact with the mark point; and
   determining the precision of the calibrator according to the second set position of the mark point and the spatial position of the contact tip,
   wherein the acquiring a spatial position of the contact tip in a case where the contact tip makes contact with the mark point comprises:
   acquiring p spatial position data of the contact tip and the mark point at multiple contact positions, wherein p is greater than or equal to four;
   using four or more spatial position data selected from the p spatial position data as fitting point data; and
   fitting the four or more fitting point data to form a virtual ball used as the spatial position of the contact tip.

5. The method according to claim 4, wherein the acquiring p spatial position data of the contact tip and the mark point at multiple contact positions comprises:
   acquiring p spatial position data, meeting a second detection deviation value, of the contact tip and the mark point at the multiple contact positions.

6. The method according to claim 4, wherein the acquiring a spatial position of the contact tip in a case where the contact tip makes contact with the mark point further comprises:
   determining spatial position data, other than the fitting point data, in the p spatial position data as detection point data;
   determining a number q of detection point data having distances to the virtual ball meeting a second preset distance threshold in the multiple detection point data;
   fitting different fitting point data selected from the p spatial position data within a second preset time period to form multiple virtual balls, and determining multiple values of q according to the multiple virtual balls and the corresponding detection point data; and
   selecting a maximum value $q_{max}$ of q from the multiple values, and determining the virtual ball corresponding to the maximum value $q_{max}$ as a standard virtual ball used as the spatial position of the contact tip.

* * * * *